(12) United States Patent
Mishima

(10) Patent No.: US 8,221,377 B2
(45) Date of Patent: Jul. 17, 2012

(54) ABSORBENT WEARING ARTICLE AND FLEXIBLE STRUCTURAL UNIT AVAILABLE THERETO

(75) Inventor: Yoshitaka Mishima, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 363 days.

(21) Appl. No.: 12/700,892

(22) Filed: Feb. 5, 2010

(65) Prior Publication Data
US 2010/0174263 A1 Jul. 8, 2010

Related U.S. Application Data

(63) Continuation of application No. 11/696,469, filed on Apr. 4, 2007, now Pat. No. 7,687,679.

(30) Foreign Application Priority Data

Apr. 5, 2006 (JP) ................................. 2006-104706

(51) Int. Cl.
A61F 13/15 (2006.01)
A61F 13/20 (2006.01)
(52) U.S. Cl. ............... 604/385.28; 604/385.19; 604/378
(58) Field of Classification Search ............ 604/385.28, 604/385.19, 378, 385.101
See application file for complete search history.

(56) References Cited

U.S. PATENT DOCUMENTS

| | | | | |
|---|---|---|---|---|
| 5,425,726 A | * | 6/1995 | Shimizu et al. | 604/385.23 |
| 5,476,457 A | * | 12/1995 | Roessler et al. | 604/364 |
| 5,643,238 A | | 7/1997 | Baker | |
| 5,776,122 A | | 7/1998 | Faulks et al. | |
| 5,817,086 A | * | 10/1998 | Kling | 604/385.19 |
| 5,853,403 A | | 12/1998 | Tanzer et al. | |
| 5,885,264 A | * | 3/1999 | Matsushita | 604/361 |
| 5,891,124 A | * | 4/1999 | Nomura et al. | 604/385.23 |
| 6,152,907 A | | 11/2000 | Widlund et al. | |
| 6,169,225 B1 | * | 1/2001 | Otsubo | 604/361 |
| 6,344,036 B1 | | 2/2002 | Ivansson | |
| 6,840,925 B2 | * | 1/2005 | Mishima et al. | 604/385.01 |
| 7,438,707 B2 | * | 10/2008 | Bushman et al. | 604/385.22 |
| 7,763,001 B2 | * | 7/2010 | Kawamura | 604/385.101 |
| 2002/0026168 A1 | | 2/2002 | Yagou et al. | |
| 2002/0173764 A1 | * | 11/2002 | Takino et al. | 604/385.28 |
| 2003/0139723 A1 | | 7/2003 | Drevik | |
| 2003/0144644 A1 | * | 7/2003 | Murai et al. | 604/385.27 |
| 2004/0039363 A1 | | 2/2004 | Sugiyama et al. | |
| 2006/0135930 A1 | * | 6/2006 | Mizutani et al. | 604/385.17 |
| 2006/0135931 A1 | * | 6/2006 | Suzuki et al. | 604/385.19 |
| 2007/0088306 A1 | * | 4/2007 | Sugiyama et al. | 604/385.19 |
| 2010/0069871 A1 | * | 3/2010 | Minato et al. | 604/385.19 |

FOREIGN PATENT DOCUMENTS

| | | |
|---|---|---|
| JP | 1-72567 | 5/1989 |
| JP | 2002-211666 | 7/2002 |
| JP | 3681320 | 5/2005 |

* cited by examiner

*Primary Examiner* — Tatyana Zalukaeva
*Assistant Examiner* — Susan Su
(74) *Attorney, Agent, or Firm* — Lowe, Hauptman, Ham & Berner, LLP

(57) ABSTRACT

An absorbent wearing article includes a liquid-absorbent structure and an excrement receiving structure having a plurality of passages defined by flexible walls formed from flexible sheets and disposed along a liquid-absorbent surface of the liquid-absorbent structure.

5 Claims, 13 Drawing Sheets side facing a wearer's skin side facing a wearer's garment

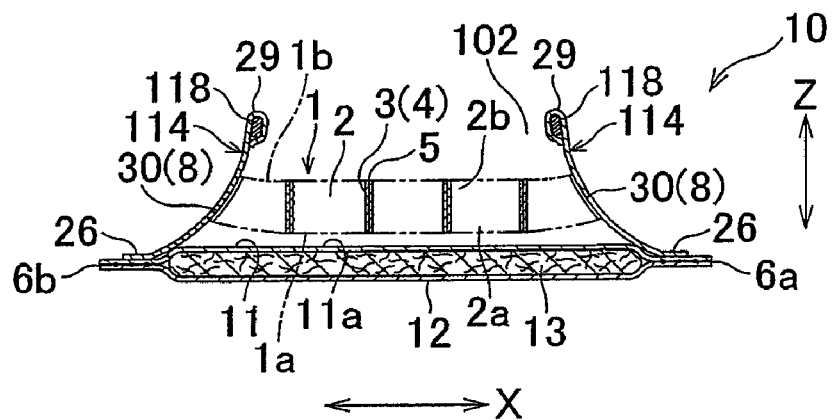
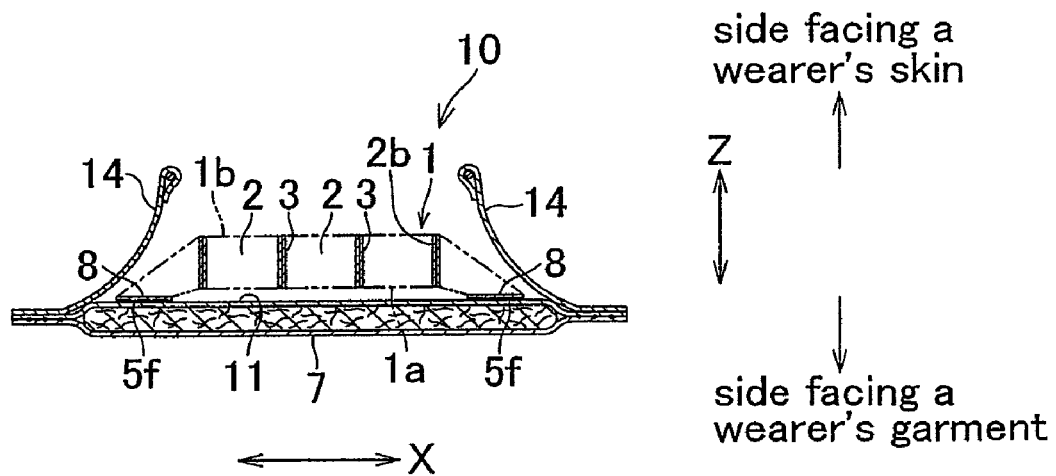

FIG.11
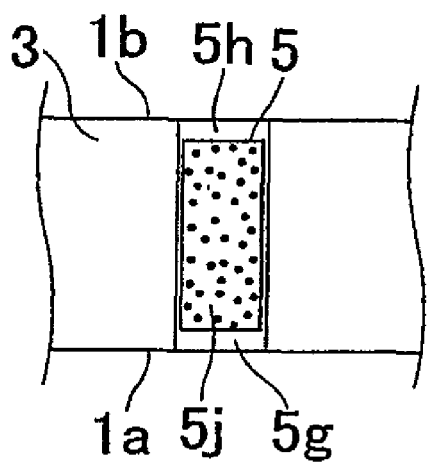
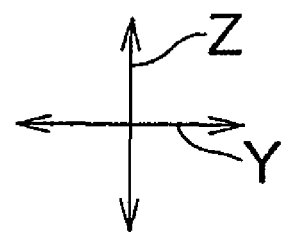
FIG.12
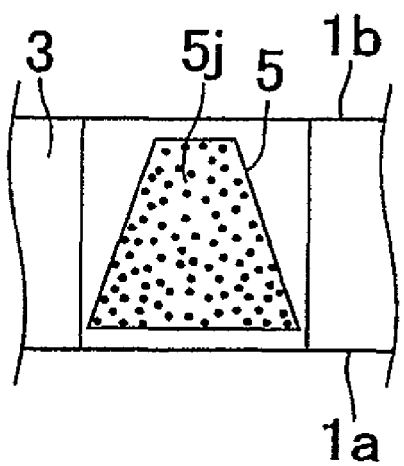
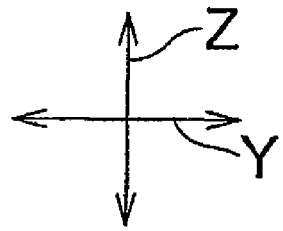

ABSORBENT WEARING ARTICLE AND FLEXIBLE STRUCTURAL UNIT AVAILABLE THERETO

RELATED APPLICATIONS

The present application is a continuation of U.S. application Ser. No. 11/696,469 filed Apr. 4, 2007, and claims priority from Japanese Application Number 2006-104706 filed Apr. 5, 2006, the disclosures of which are hereby incorporated by reference herein in their entirety.

BACKGROUND OF THE INVENTION

The present invention relates generally to absorbent wearing articles such as disposable diapers, disposable sanitary napkins, liquid-absorbent incontinence pads and the like. The present invention also relates to flexible structural units available to the absorbent article.

It is well known in the art that absorbent wearing articles (hereinafter referred to as "article") intending to prevent a wearer's skin being soiled with bodily discharges such as loose feces by attaching a panel having a plurality of openings to an inner sheet. For example, the article disclosed in Japanese Patent Publication No. 3681320 (hereinafter referred to as "REFERENCE") comprises an inner sheet, an outer sheet and a liquid-absorbent core sandwiched between these top- and outer sheets. Configurationally, this article has longitudinally a front region, a rear region and an intermediate region extending between these front and rear regions. In the rear region and the intermediate region, the panel formed from a fibrous web is attached to the outer surface of the inner sheet. The panel has a plurality of openings extending through the fibrous web in its thickness direction and walls in a direction orthogonal to the thickness direction and barriers defining the respective openings wherein a fibrous density of the respective barriers is set to be gradually increased upward from the side of the inner sheet.

In the case of the wearing article disclosed in REFERENCE, watery bowel movement or loose passage flows into the openings and then solid ingredients of the watery bowel movement permeate into a low density fibrous layer, and thereby the wearer's skin can be prevented being soiled with watery bowel movement. However, in order to assure a desired mechanical strength of the panel, the barriers defining the respective openings should have thickness above a certain level. Consequently, the open area ratio of the openings has been limited to 80% or less. Additionally, it is necessarily difficult for the panel formed the fibrous web to be readily deformed in response to movement of the wearer's crotch region and often gaps have been left around the wearer's legs, causing undesirable leakage.

SUMMARY OF THE INVENTION

In view of the problem as has been described above, it is an object of the present invention to provide an absorbent wearing article provided with an excrement receiving structure adapted to achieve a high open area ratio, to be readily deformed in response to motions of the wearer, and to prevent a wearer's skin being soiled with excrement. It is another object of the present invention to provide a flexible structural unit to be used for the excrement receiving structure.

The present invention is including a first invention and a second invention.

According to the first invention, there is provided an improvement in the absorbent wearing article having a longitudinal direction, a transverse direction and a thickness direction, comprising:

a front waist region, a rear waist region and a crotch region therebetween;

an excrement receiving structure at least in the crotch region of the front and rear waist regions and the crotch region;

and a liquid-absorbent structure having a liquid-absorbent surface.

The improvement according to the first invention further comprises the excrement receiving structure having a plurality of passages of conduit-type defined by flexible walls formed from flexible sheets with surfaces of the flexible sheets opposed to each other wherein each of the plurality of passages has a first opening facing the liquid-absorbent surface and a second opening facing a wearer's skin.

The first invention may include the following preferred embodiments.

The embodiment wherein the excrement receiving structure is supported along the liquid-absorbent surface so as to be separatable from the liquid-absorbent surface in the thickness direction.

The embodiment wherein the excrement receiving structure is continuously or intermittently fixed at least at opposite peripheral edge zones in the longitudinal direction or at least at opposite peripheral edge zones in the transverse direction to the liquid-absorbent surface.

The embodiment wherein the excrement receiving structure is provided with a structure that each paired flexible sheet strips extend in a first direction with surfaces of each paired flexible sheet strips opposed to each other in a second direction, having each pair of V-shaped portions symmetrically opposed to each other in the second direction, arranged in a zigzagged manner in the first direction of each flexible sheet strip, open end portions of each pair of the V-shaped portions adjacent to each other in the second direction are connected to each other, and thereby the flexible walls define the plurality of passages.

The embodiment wherein closed portions of each pair of the V-shaped portions adjacent to each other in the second direction are connected to each other by any one of a bonded portion between the pair of flexible sheet strips and a bridge portion of flexible sheet between the paired flexible sheet strips.

The embodiment wherein a thickness dimension of each of the flexible walls is smaller than a length dimension of each of the flexible walls in the thickness direction.

The embodiment wherein the length dimension of each of the flexible walls in the thickness direction is about 5-30 mm.

The embodiment wherein the first direction corresponds to the longitudinal direction and the second direction corresponds to the transverse direction.

The embodiment wherein a ratio of an area occupied by at least the second openings of the first and second openings of the plurality of passages is 80% and more.

The embodiment wherein the article further comprises a pair of leak-barrier cuffs extending along lateral edges of the excrement receiving structure in the longitudinal direction, the excrement receiving structure is supported by the pair of leak-barrier cuffs at least in vicinities of the lateral edges.

The embodiment wherein the pair of leak-barrier cuffs have proximal edges secured in the vicinities of the lateral edges and elasticized distal edges, the excrement receiving structure being between the proximal and distal edges.

The embodiment wherein the liquid-absorbent structure comprises a liquid-pervious inner sheet defining the liquid-absorbent surface, a liquid-impervious outer sheet facing the wearer's garment and a liquid-absorbent core interposed between the inner and outer sheets.

According to the second invention of the present invention, there is provided a flexible structural unit having passages of conduit-type for fluids.

The flexible structural unit according to the second invention has a plurality of passages defined by flexible walls formed from flexible sheets with surfaces of the flexible sheets opposed to each other wherein each of the plurality of passages has a first opening and a second opening opposite to the first opening in the height direction of the flexible walls.

The second invention may include the following preferred embodiments.

The embodiment wherein the flexible structural unit is provided with a structure that each paired flexible sheet strips extend in a first direction with the surfaces of each paired flexible sheet strips opposed to each other in a second direction, having each pair of V-shaped portions symmetrically opposed to each other in the second direction, arranged in a zigzagged manner in the first direction of each flexible strip, open end portions of each pair of the V-shaped portions adjacent to each other in the second direction are connected to each other, and thereby the flexible walls are defining the plurality of passages.

The embodiment wherein the flexible structural unit is extendable and contractible at least in one direction of the first direction and the second direction.

The flexible walls constituting the excrement receiving structure in the according to the first invention are formed from flexible sheets with surfaces of the flexible sheets opposed to each other, thereby an open area ratio becomes higher than that of prior art and, in addition, the excrement receiving structure can deform readily in response to motions of the wearer, the leakage of excrement from the gaps between the article and the wearer's legs can be avoided. Furthermore, the excrement receiving structure is interposed between the wearer's body and excrement to prevent the wearer's skin being soiled with excrement. The flexible walls constituting the excrement receiving structure are appropriately buckled or bent as the wearer's buttocks bear down on the excrement receiving structure so as to cover excrement and thereby present the wearer's skin being soiled with excrement.

According to the embodiments wherein the excrement receiving structure is supported along the liquid-absorbent surface so as to separatable from the liquid-absorbent surface in the thickness direction or the excrement receiving structure is fixed at peripheral edge zones in any of the longitudinal direction and the transverse direction to the liquid-absorbent surface, the excrement receiving structure is free from the liquid-absorbent surface except for the zones not fixed to the liquid-absorbent surface, so that excrement can flow or drift between the liquid-absorbent surface and the excrement receiving structure. Therefore, excrement does not stay locally on the liquid-absorbent surface, and the entire liquid-absorbent surface can be utilized for absorption of the water contained in excrement.

According to the embodiment wherein the flexible walls are formed from the flexible sheet strips, it is easily possible to form the flexible/soft and thin excrement receiving structure by bonding a plurality of stacked flexible sheet strips.

According to the embodiment wherein a length dimension of the flexible walls is 3-30 mm, it is possible to minimize soiling the wearer's skin due to excrement received by the excrement receiving structure flowing back to the side of the wearer's skin.

According to the embodiment wherein the excrement receiving structure is supported by the leak-barrier cuffs, the excrement receiving structure is supported at predetermined height from the liquid-absorbent surface of the liquid-absorbent structure and thereby it is possible to maintain a opened state of the plurality of passages.

According to the second invention of the present invention, there is provided a flexible structural unit having a plurality of passages of conduit-type which is adapted to allow fluids such as loose feces to flow therethrough and is applicable to an absorbent wearing article according to the first invention.

BRIEF DESCRIPTION OF THE DRAWINGS

FIG. 7 is a cut surface taken along the line VII-VII in FIG. 6;

FIG. 8 is a cut surface similar to FIG. 4 to illustrate an embodiment of the present invention;

FIG. 11 is a sectional view taken along the line XI-XI in FIG. 10;

FIG. 12 is a sectional view similar to FIG. 11 to illustrate an embodiment of the present invention;

DETAILED DESCRIPTION OF THE PREFERRED EMBODIMENTS

Details of an absorbent wearing article (hereinafter referred to "article") and a flexible structural unit therefor according to the present invention will be more fully understood from the description of disposable diapers as embodiments given hereunder with reference to the accompanying drawings. In Figs., a transverse direction is indicated by an arrow X, a longitudinal direction is indicated by an arrow Y, a thickness direction is indicated by an arrow Z.

Figure 1:
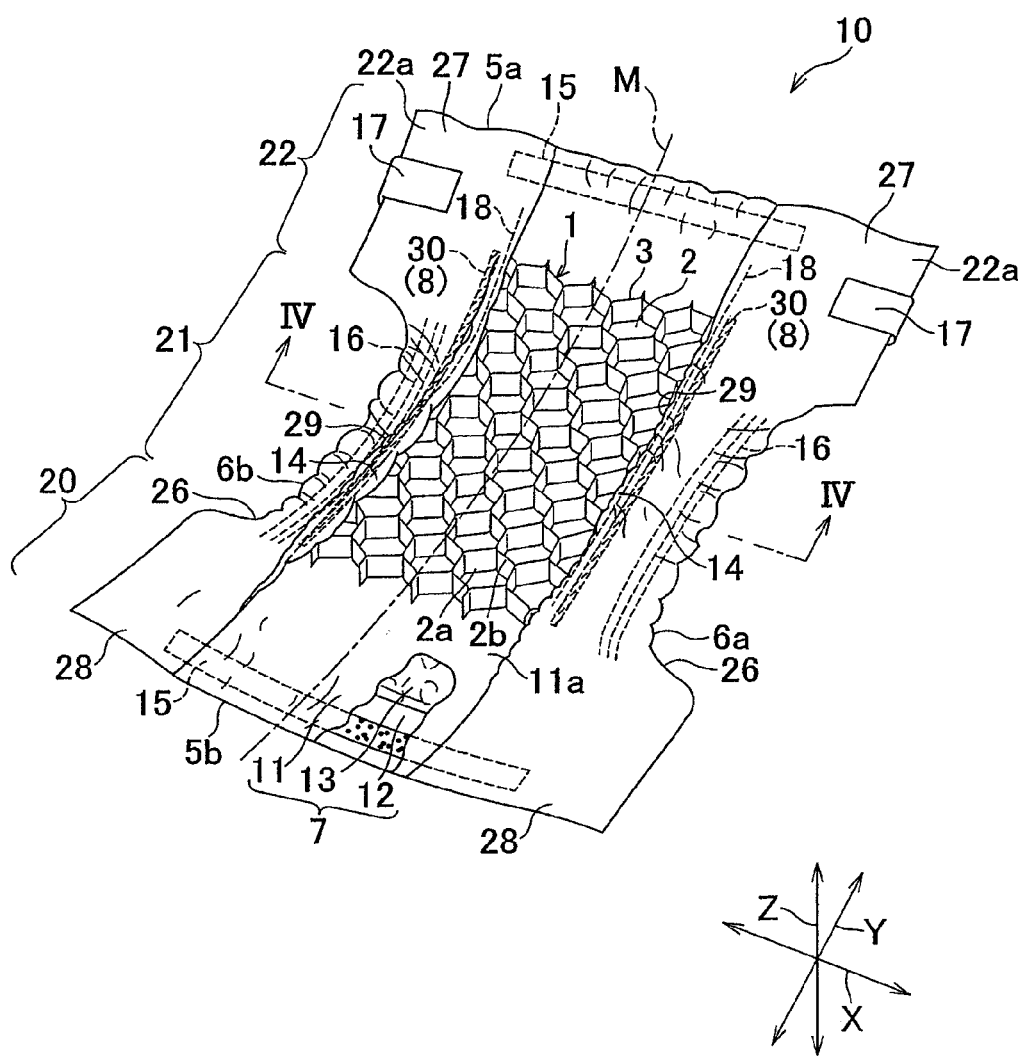
FIG. 1 is a perspective view, partially cutaway, showing a disposable diaper according to a first embodiment of the present invention.

FIG. 1 is a partially cutaway perspective view showing a disposable diaper 10 (hereinafter referred to as "diaper") as developed and viewed from the side of the wearer's skin. The diaper 10 according to the present invention comprises an excrement receiving structure 1, a liquid-absorbent structure 7 and a pair of leak-barrier cuffs 14. The absorbent structure 7 comprises a liquid-pervious inner sheet 11 defining a liquid-absorbent surface 11a and facing the side of the wearer's skin (not shown), a liquid-impervious outer sheet 12 facing the wearer's garment (not shown) and a liquid-absorbent core 13 interposed between the inner and outer sheets 11, 12. The liquid-absorbent core 13 is covered with a liquid-absorbent sheet (not shown) such as tissue papers and tissue fibrous nonwoven fabrics and permanently bonded to at least one of the inner and outer sheets 11, 12 via the liquid-absorbent sheet.

The diaper 10 has a front waist region 20, a rear waist region 22 and a crotch region 21 extending between the front and rear waist regions 20,22 and its longitudinal direction is indicated by an arrow Y, its transverse direction is indicated by an arrow X and its thickness direction is indicated by an arrow Z.

As stock materials for the inner sheet 11, liquid-pervious sheets such as hydrophilic fibrous nonwoven fabrics or apertured plastic films may be used. As stock materials for the outer sheet 12, on the other hand, breathable and liquid-impervious sheets such as hydrophobic fibrous nonwoven fabrics, liquid-impervious plastic films or a laminate of the nonwoven fabric and the film may be used. The liquid-absorbent core 13 comprises a mixture of fluff pulp fibers, superabsorbent polymer particles, and optionally thermoplastic resin fibers etc. which is compressed together to a desired thickness.

Along a rear end 5a extending across the rear waist region 22 in the transverse direction X and a front end 5b extending across the front waist region 20 in the transverse direction X of the diaper 10, strip-shaped waist elastic members 15 are attached in a stretched state, to the diaper 10 between the inner sheet 11 and the outer sheet 12. In vicinities of lateral edges 6a, 6b of the diaper 10, a plurality of leg elastic members 16 extending in a leg-encircling direction are attached in a stretched state, to the diaper 10 between the inner sheet 11 the outer sheet 12. The elastic members 15, 16 are elastically contractible in their longitudinal directions.

The rear waist region 22 is provided on ears 22a thereof with tape fasteners 17 adapted to be unfolded outward while the outer sheet 12 in the front waist region 20 is provided on an outer surface thereof with a target tape (not shown) serving as a landing zone for the tape fasteners 17. When the diaper 10 is put on the wearer, the diaper 10 is curved with the inner sheet 11 inside and the tape fasteners 17 may be releasably anchored on the target tape to form a waist-hole and a pair of leg-holes (not shown).

The pair of leak-barrier cuffs 14 are symmetrical to each other about a longitudinal center line M extending on the inner sheet 11 between the front and rear waist regions 20, 22 so as to bisect a width of the diaper 10 and extend in the longitudinal direction Y, leaving a predetermined space therebetween. Proximal edges 26 of the respective leak-barrier cuffs 14 lying on the sides away from the longitudinal center line M are permanently attached to the inner sheet 11 along the lateral edges 6a, 6b. Rear ends 27 of the respective leak-barrier cuffs 14 lying in the rear waist region 22 as well as front ends 28 lying in the front waist region 20 are also permanently attached to the inner sheet 11. The predetermined space between the pair of leak-barrier cuffs 14 may be dimensioned sufficiently to cover the wearer's excretory organ.

The leak-barrier cuffs 14 are not bonded to the inner sheet 11 in regions other than the zones having been described above. Distal edges 29 of the respective leak-barrier cuffs 14 lying more close to the longitudinal center line M are respectively provided elastic members 18 exclusively for the leak-barrier cuffs 14 so that these elastic members 18 are permanently attached to the respective distal edges 29 and wrapped with the distal edges 29. With such a construction, the elastic members 18 for the leak-barrier cuffs contract whereupon the distal edges 29 are spaced apart from the inner sheet 11 in the thickness direction Z as the diaper 10 is curved with the inner sheet 11 inside for actual use of the diaper 10 and consequently the leak-barrier cuffs 14 rise up on the inner sheet 11, i.e., on the liquid-absorbent surface 11a under the effect of elastic contraction.

In the excrement receiving structure 1 is provided with a plurality of passages 2 of conduit-type penetrating the excrement receiving structure 1 in the thickness direction thereof. The passages 2 are defined by flexible walls 3 formed from flexible/soft and thin sheets and having a lower opening 22a facing the liquid-absorbent surface 11a of the inner sheet 11 and an upper opening 22b facing the wearer's skin. The passages 2 allow fluids such as loose feces to flow through from the upper opening 2b to the lower opening 2a. The excrement receiving structure 1 overlies the liquid-absorbent surface 11a of the inner sheet 11 at least in a part of the crotch region 21, preferably the liquid-absorbent surface 11a between the rear waist and crotch regions 21, 22, and the excrement receiving structure 1 is separable from the absorbent surface 11a in the thickness direction Z. Expression used herein "the excrement receiving structure 1 can become free from the inner sheet 11" means that, although the excrement receiving structure 1 may be partially come in contact with or bonded to the inner sheet 11, the remaining portions are free from the inner sheet 11 so as to leave a gap between the excrement receiving structure 1 and the inner sheet 11.

Lateral edges 8 of the excrement receiving structure 1 are permanently bonded to and supported by respective surfaces of the leak-barrier cuffs 14 facing the inner sheet 11 at respective attachment zones 30 extending in the longitudinal direction Y. It should be noted here that the excrement receiving structure 1 is not bonded to the inner sheet 11 and free from the liquid-absorbent surface 11a of the inner sheet 11 so that the excrement receiving structure 1 may be separatable from the absorbent surface 11a in the thickness direction Z.

Figure 2:
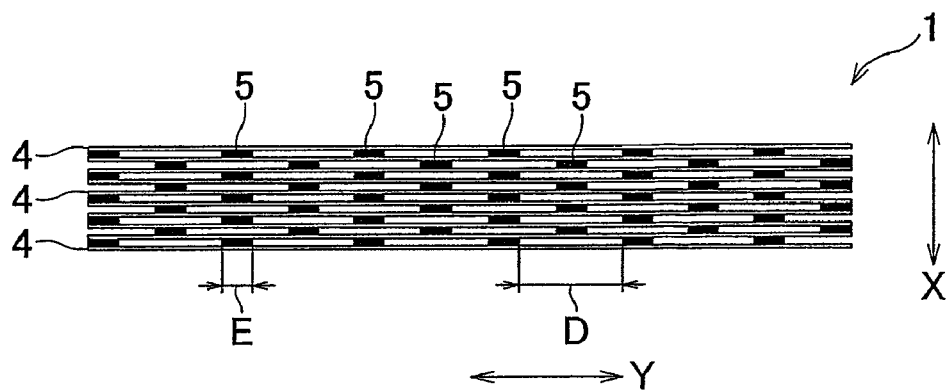
FIG. 2 is a schematic diagram illustrating a method for making an excrement receiving structure.
Figure 3:
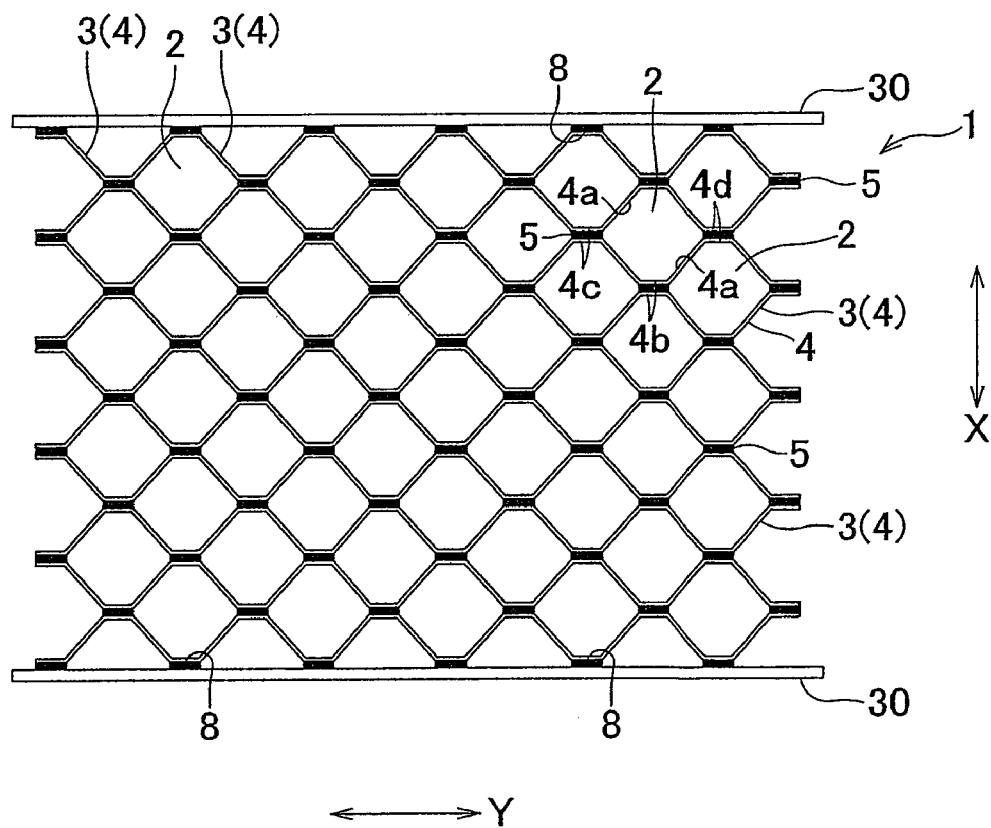
FIG. 3 is a plan view illustrating the method for making the excrement receiving structure.

FIGS. 2 and 3 are a schematic diagram and a plan view of the excrement receiving structure 1 illustrating a method for forming the excrement receiving structure 1. FIG. 2 shows the excrement receiving structure before it is extended and FIG. 3 shows the excrement receiving structure 1 after it has been extended, respectively.

As will be understood from FIGS. 2 and 3, a method for forming the excrement receiving structure 1 comprises the steps of:

stacking a plurality of the flexible sheet strips 4 formed from fibrous nonwoven fabrics each having a predetermined width, bonding a fist pair of flexible sheet strips 4 extending in the longitudinal direction Y and adjacent to each other in a stacked direction, i.e., in the transverse direction X, at a first plurality of bonding spots 5 arranged at regular intervals in the longitudinal direction Y to each other, bonding a second pair of flexible sheet strips 4 one of which is adjacent to the first pair of flexible sheet strips 4 in the transverse direction X and extending in the longitudinal direction Y to each other, at a plurality of the second bonding spots 5 arranged at regular intervals in the longitudinal direction Y so that each of the second plurality of bonding spots 5 may located between each of the first plurality of bonding spots 5, further, bonding the remaining flexible sheet strips 4 to each other in the manner mentioned above, and lastly, expanding the plurality of bonded flexible sheet strips 4 in the stacked direction, i.e., in the transverse direction X and thereby forming the flexible walls 3 while defining the plurality of passages 2 by portions of the plurality of bonded flexible sheet strips 4 between each of the first plurality of bonding spots 5 and between each of the second plurality of bonding spots 5.

The excrement receiving structure 1 thus formed, is provided with a structure that each paired flexible sheet strips 4 extend in the longitudinal direction Y with the surfaces of each paired flexible sheet strips 4 opposed to each other in the transverse direction X, having each pair of V-shaped portions 4a symmetrically opposed to each other in the transverse direction X and arranged in a zigzagged manner in the longitudinal direction Y, open end portions 4c, 4c, 4d, 4d of each pair of the V-shaped portions adjacent to each other in the transverse direction X being bonded by the plurality of bonding spots 5, and thereby the flexible walls 3 defining the plurality of passages 2. Closed portions 4b of each pair of the V-shaped portions adjacent to each other in the transverse direction X are also bonded by the bonding spots 5. Such excrement receiving structure 1 has a honeycomb-like structure or a net-like structure as viewed from above.

Figure 19:
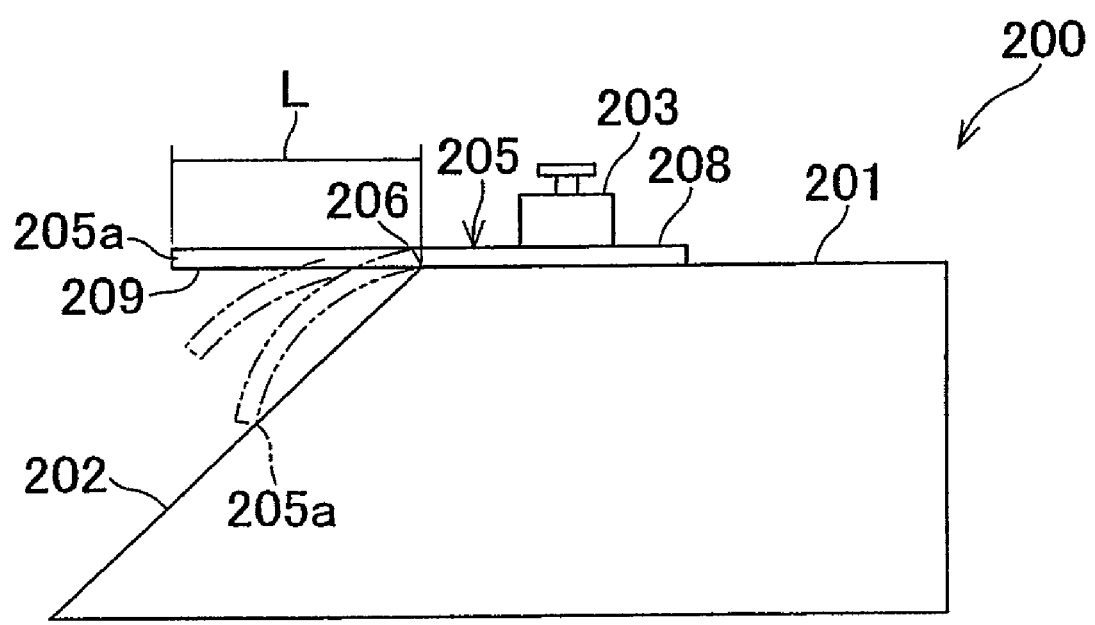
FIG. 19 is a side view of an apparatus to measure a flexural rigidity of a sheet.

Each of the flexible sheet strips 4 preferably has a bending flexural stiffness (as measured by a cantilever method using an apparatus 100 in FIG. 19) of about 150 mm or less and a thickness dimension of each of the flexible sheet strips 4 preferably is smaller than a width dimension of the flexible sheet strip 4, i.e., a length dimension of the flexible wall 3 in the thickness direction Z. Specifically, the thickness dimension of the flexible sheet strip 4 preferably is about 5 mm or smaller, and if the bending resistance exceeds about 150 mm, the excrement receiving structure 1 may not be readily deformed in response to motions of the wearer. The thickness dimension of the flexible sheet strips 4 may be set to about 5 mm or smaller, more preferably to about 2 mm or smaller to obtain the excrement receiving structure 1 of a high open area ratio. Although the minimum value of the thickness dimension is not specified, the minimum value may be preferably set to about 0.1 mm to 2 mm from the viewpoint of manufacturing cost. A width dimension of the flexible sheet strip 4, i.e., length dimension of the flexible wall 3 depends on a physical size of the wearer and a particular aspect of excrement. For example, in the case of the diaper 10, the width dimension of the flexible sheet strip 4 is preferably in a range of about 5 to about 30 mm, more preferably about 10 to about 20 mm. If the width dimension of the flexible sheet strip 4 is less than such a range, the flexible wall 3 may not cover excrement sufficiently. Consequently, it will become difficult to prevent the wearer's skin being soiled with excrement. If the width dimension exceeds the range as has been described, on the other hand, the excrement receiving structure 1 may be always bent between the inner sheet 11 and the wearer's skin and, in consequence, the area of the respective passages 2 may be unacceptably reduced for smooth passage of excrement such as feces. According to this embodiment, each of the flexible sheet strips 4 has a width dimension of about 15 mm. Preferably, the width dimension of the flexible sheet strip 4 is arranged to avoid to close the passage 2 by the flexible sheet strip 4 when the flexible sheet strip 4 is collapsed under a body pressure.

According to this embodiment, a spunbonded nonwoven fabric made of polypropylene fibers having a thickness dimension of about 0.18 mm is used as stock materials for the flexible sheet strips 4. This spunbonded flexible sheet strip 4 is air-permeable and liquid-impervious and capable of recovering from a compressed state. It should be understood that the component fibers of this flexible sheet strip 4 is not limited to the polypropylene fibers and it is possible to use other fibers such as polypropylene/polyester composite fibers, polyester-based fibers, polyamide-based fibers polyurethane-base fibers and so on. Regarding processes for making such nonwoven fabrics, it is possible to use conventional processes such as a needle punching process, a melt blowing process, a thermal bonding process, a chemical bonding process or an air-through process. If the flexible sheet strip 4 is made of crimped fibers or elastic fibers, the flexible sheet strip 4 is elastically stretchable and contractible and the excrement receiving structure 1 has little wrinkles even if it is folded.

Each pair of the adjacent flexible sheet strips 4 may be bonded to each other by hot melt adhesives. However, it is also possible to use any well known techniques such as heat seal or ultra-sonic seal. According to this embodiment, a distance D between each pair of the adjacent bonding spots 5 on one and same sheet strip 4 is set to about 25 mm and a length dimension E of the bonding spot 5 is set to 5 mm in the longitudinal direction Y. The distance D between each pair of the adjacent bonding spots 5 in the longitudinal direction Y also depends on the wearer's physical size and the aspect of excrement. Furthermore, it is unnecessary for the distance D between each pair of the adjacent bonding spots 5 to be uniform and, for example, the excrement receiving structure 1 may have, in one region, the bonding spots 5 whose distance D is set to be larger than the distance D set in other regions to form the correspondingly larger passages 2 in the one regions than in the other regions. In this case, the region in which the larger passages 2 are formed may be located in the crotch region 21 of the diaper 10 so as to be opposed to the wearer's anus to ensure that non-loose feces can reach the inner sheet 11 without staying on the excrement receiving structure 1.

The flexible sheet strips 4 stacked on upon another as illustrated in FIG. 2 may be expanded in the transverse direction X to obtain the excrement receiving structure 1 formed with a plurality of the passages 2 defined by the flexible walls 3 and having the openings 2a, 2b. Then the lateral edges 8 of the excrement receiving structure 1 extending in the longitudinal direction Y may be permanently bonded to the attachment zones 30 of the respective leak-barrier cuffs 14 to ensure that the excrement receiving structure 1 is supported by the leak-barrier cuffs 14 with a plurality of the passages 2 maintained in an opened states, respectively. As will be seen in FIG. 3, the lateral edges 8 of the excrement receiving structure 1 are bonded to the respective attachment zones 30 at the bonding spots 5 arranged at regular intervals by hot melt adhesives or the like.

Since the flexible walls 3 of the excrement receiving structure 1 are defined by the flexible and thin sheet strips 4 whose width direction is coincident with the thickness direction Z and the open area ratio of the excrement receiving structure 1 depends on the thickness of the flexible sheet strips 4, the present invention provides the excrement receiving structure 1 with a high open area ratio if the thickness is reduced. According to this embodiment, as have been described above, the open area ratio can be approximately 98%, although the open area ratio depends on the number of the passages 2 per unit area of the excrement receiving structure 1. In this way, the excrement receiving structure 1 according to the invention can easily achieve the open area ratio exceeding 80% which has conventionally been difficult to achieve so far as panels formed from conventional fibrous webs are used. The term "open area ratio" used herein refers to a ratio of the area occupied by each of the upper openings 2b of the lower and upper openings 2a, 2b of the passages 2 per unit area of the excrement receiving structure 1. A diameter of each the passages 2 may be gradually small from the upper opening 2b toward the lower opening 2a. Such a configuration of the passages 2 may prevent excrement flowed on the liquid-absorbent surface 11a of the inner sheet 11 flowing back to the side of the upper openings 2b.

Figure 4:
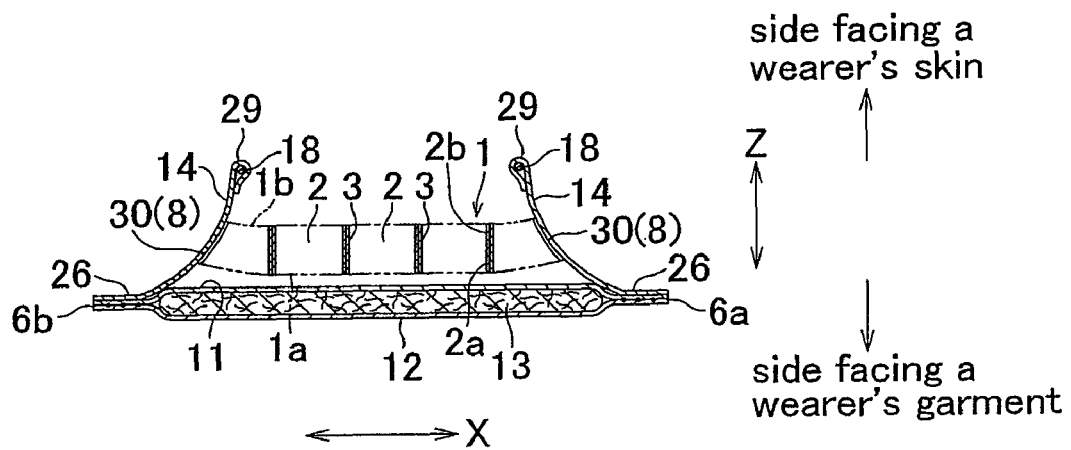
FIG. 4 is a cut surface taken along the line IV-IV in FIG. 1.
Figure 5:
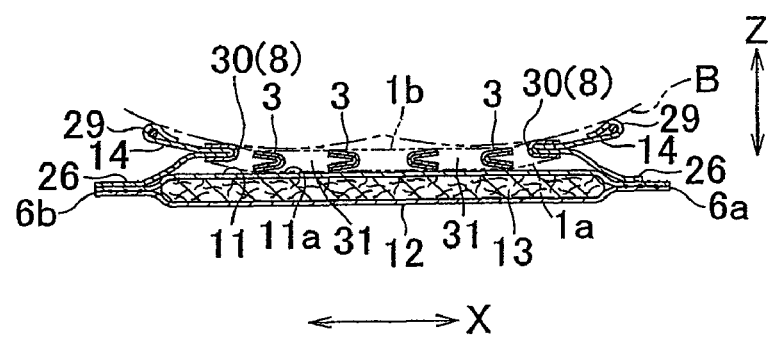
FIG. 5 is a schematic diagram illustrating a condition in which buttocks of a wearer bear down upon the diaper.

Now a functional effect of the diaper 10 provided with the excrement receiving structure 1 will be described with reference to FIGS. 4 and 5. FIG. 4 is a cut surface taken along the line IV-IV in FIG. 1 showing the diaper 10 put on the wearer's body and FIG. 5 is a schematic diagram illustrating the diaper 10 when the wearer's buttocks bear down thereon. In FIGS. 4 and 5 the lower surface 1a and the upper surface 1b of the excrement receiving structure 1 are shown by imaginary lines.

The passages 2 of the excrement receiving structure 1 extend in a direction generally vertical to the liquid-absorbent surface 11a of the inner sheet 11. The attachment zones 30 are located on the leak-barrier cuffs 14 between the proximal edges 26 and the distal edges 29 thereof, and do not interrupt shrinkages of the elastic members 18 of the leak-barrier cuffs. With such an arrangement, it is unlikely that excrement might leak out from the diaper even if the region defined between the attachment zone 30 and the distal edge 29 in each of the leak-barrier cuffs 14 comes in contact with the wearer's skin. The excrement receiving structure 1 is not bonded to the inner sheet 11 and capable of being apart from the inner sheet 11.

Excrement or excreta such as feces or urine reach the liquid-absorbent surface 11a of the inner sheet 11 through the passages 2 and the water contained therein is absorbed by the liquid-absorbent core 13. The residue (solid constituent) is left on the inner sheet 11 after the water has been absorbed, but isolated from the wearer's skin by the excrement receiving structure 1 and consequently the wearer's skin is not soiled with the residue.

The excrement receiving structure 1 is free from the inner sheet 11, as has been described above, so that excrement can flow or drift between the inner sheet 11 and the excrement receiving structure 1. Therefore, excrement does not stay locally on the inner sheet 11, and the entire liquid-absorbent surface 11a of the inner sheet 11 can be utilized for absorption of the water contained in excrement. Particularly in the case of loose feces, the water contained herein can be rapidly absorbed to leave the solidified excrement on the inner sheet 11 and such solidified excrement can be isolated from the wearer's skin by the excrement receiving structure 1.

The excrement receiving structure 1 is formed from the flexible and thin sheet strips 4 and therefore the structure 1 itself is soft and can be deformed in response to motions of the wearer's crotch region. When elastic members of the diaper 10 contracts, the elastic members cause the diaper 10 to contract in the transverse direction X and/or in the longitudinal direction Y. The elastic members will also cause the excrement receiving structure 1 to contract. However, when the excrement receiving structure 1 contracts, there are no wrinkles on the upper surface 1b of the excrement receiving structure 1, although the shapes of the passages 2 changes. In this way, there is unlikely that undesirable gaps and/or wrinkles might be formed around the leg-holes and other areas of the diaper 10 and excrement leaks through these gaps and/or wrinkles can be prevented.

Since the excrement receiving structure 1 is appropriately flexible wall 3 are buckled or bent to some degree when the wearer's buttocks B bear downward on the excrement receiving structure 1 as indicated by imaginary lines in FIG. 5. And then excrement such as loose feces on the inner sheet 11 may be covered with the flexible walls 3 and retained in spaces 31 defined each pair of the adjacent buckled flexible walls 3. As a result, the excrement receiving structure 1 prevents the wearer's skin being soiled with excrement. In this situation, the excrement receiving structure 1 is provided preferably in the manner that the flexible sheet strips 4 forming the flexible walls 3 have the fiber orientation generally vertical to the liquid-absorbent surface 11a of the inner sheet 11. The fiber orientation of the flexible sheet strips 4 selected in this manner ensures that the flexible sheet strips 4 have a relatively high stiffness in the direction of this fiber orientation and the flexible walls 3 are appropriately buckled or bent so as to leave the desired spaces 31. Flexibility of the excrement receiving structure 1 ensures also that the wearer is free from any feeling of discomfort even when the wearer's buttocks B bear down on the excrement receiving structure 1. A flexible panel of nonwoven fabric which has a plurality of such conduits as the passage 2 provided by the excrement receiving structure 1 may be utilized in various articles other than the absorbent wearing article according to the present invention.

Figure 6:
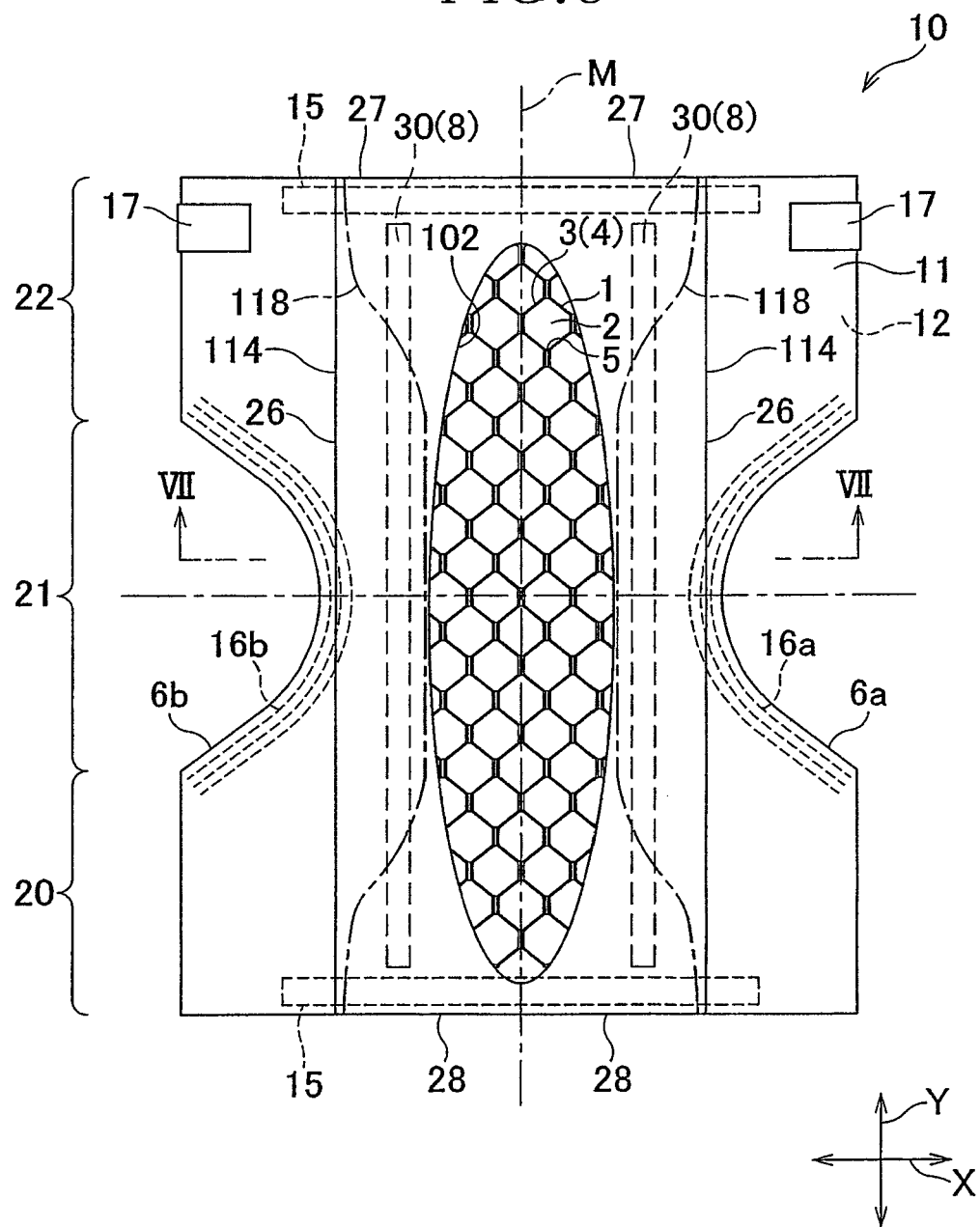
FIG. 6 is a plan view showing the diaper according to a second embodiment of the present invention as viewed from an inner side thereof.

Now a second embodiment will be described with reference to FIGS. 6 and 7. FIG. 6 is a plan view of an extended diaper 10 according to the second embodiment of the present invention as viewed from the front side of the inner sheet 11 and FIG. 7 is a cut surface taken along the line VII-VII in FIG. 6.

The diaper 10 according to this second embodiment is distinguished from the diaper 10 according to the first embodiment in that a leak-barrier sheet 114 is used in place of the paired leak-barrier cuffs 14. In the following description, duplicating aspects with respect to the first embodiment will be simplified as far as possible.

The leak-barrier sheet 114 comprises a nonwoven fabric and corresponds generally to the pair of the leak-barrier cuffs 14. The leak-barrier sheet 114 is elastically stretchable/contractible in the transverse direction X and attached in a stretched state to the inner sheet 11 so as to extend from the rear waist region 22 to the front waist region 20 in a symmetrical relationship with each other about the longitudinal center line M and to form an opening 102 tapering from the crotch region 21 to the front and rear waist regions 20, 22.

The leak-barrier sheet 114 is permanently attached to the inner sheet 11 along the respective proximal edges 26 and at the respective rear and front ends 27, 28. The leak-barrier sheet 114 is further provided with a pair of elastic members 118 extending in a symmetrical relationship with a pair of each other about the longitudinal center line M as indicated by a thick chain line. The elastic members 118 are attached in a stretched state to the leak-barrier sheet 114 so as to extend in the longitudinal direction in parallel to the longitudinal center line M in the crotch region 21 and extend from the crotch region 21 to the respective proximal edges 26. In this way, the elastic members 118 keep the opening 102 opened.

The excrement receiving structure 1 is permanently bonded to the surfaces of the leak-barrier sheet 114 opposed to the inner sheet 11 in the respective attachment zones 30. The excrement receiving structure 1 is not bonded to the inner sheet 11 and therefore separable from the inner sheet 11. The excrement receiving structure 1 as well as the attachment zones 30 is the same as those in the first embodiment.

When the diaper 10 is curved with the inner sheet 11 inside in order to put on it, the leak-barrier sheet 114 is spaced apart from the inner sheet 11 in the thickness direction Z under the effect of elastic contraction of the traverse elastic members 118 and rise up on the inner sheet 11.

FIG. 7 is a cut surface taken along the line VII-VII in FIG. 6, but the lower surface 1a and the upper surface 1b of the excrement receiving structure 1 are sown by imaginary lines and the leak-barrier sheet 114 is rising up on the inner sheet 11. As will be understood from FIG. 7, the passage 2 of the excrement receiving structure 1 attached to the leak-barrier sheet 114 in the respective attachment zones 30 have orientation generally vertical to the liquid-absorbent surface 11a of the inner sheet 11. Elastically stretchable/contractile properties of the leak-barrier sheet 114 in the transverse direction X serves to further open out the passages 2 of the excrement receiving structure 1.

Excrement or excreta such as feces or urine reach the liquid-pervious inner sheet 11 through the passages 2 and then the water contained therein is absorbent by the liquid-absorbent core 13. Residue (solid substance) left after the water absorption is isolated by the excrement receiving structure 1 from the wearer's skin which is, in turn, effectively prevents the wearer's skin being soiled with such residue.

The excrement receiving structure 1 is separable from the inner sheet 11 as has previously been described, therefore excrement can smoothly drift between the excrement receiving structure 1 and the inner sheet 11 and the water contained therein is reliably absorbed by the liquid-absorbent core 13. Furthermore, the excrement receiving structure 1 is adequately flexible to be deformed in response to motions of the wearer's crotch region. In this way, there is unlikely that undesirable gaps are made between the diaper 10 and wearer's legs causing undesirable leakage. In addition, even when the wearer's buttocks (not shown) bear down on the excrement receiving structure 1, the flexible walls 3 are appropriately buckled or bent not only to cover excrement but also to retain excrement in spaces created among the buckled flexible walls 3. In this way, the excrement receiving structure 1 prevents the wearer's skin being soiled excrement.

While the present invention has been described on the basis of two particular embodiments, it will be appreciated by those skilled in the art that the present invention is not limited to the disposable diaper 10 but may be applicable also for sanitary napkins and incontinence pads. The excrement receiving structure 1 may be formed also using liquid-pervious nonwoven fabrics. For example, when the liquid impervious nonwoven fabric 4 is used for the excrement receiving structure 1, discharged feces, particularly watery bowel movement can be more effectively prevented from soiling the wearer's skin. When the liquid-pervious nonwoven fabric 4 is used, the excrement receiving structure 1 itself contributes to rapid absorption of the water contained in excrement.

It is also possible to make the excrement receiving structure 1 using stretchable/contractile nonwoven fabrics. Alternatively, the excrement receiving structure 1 may be formed from flexible plastic films or flexible resinous foams rather than nonwoven fabrics. It is also possible to provide the liquid-absorbent structure 7 covered with no inner sheet. In the second embodiment also, the circular inner edge of the leak-barrier sheet 114 may be provided with elastic members extending along the circular inner edge.

Although not shown in Figs., the excrement receiving structure may be continuously or intermittently fixed at least at opposite edge zones in the longitudinal direction Y or at least at opposite edge zones in the transverse direction X of a peripheral edge of the excrement receiving structure 1 to the liquid-absorbent surface 11a of the liquid-absorbent structure 7. In this case, similarly to the foregoing embodiments of the present invention, the excrement receiving structure 1 is spaced apart upwardly from the liquid-absorbent surface 11a except the zones of the excrement receiving structure 1 fixed thereto when the diaper 10 is worn with the liquid-absorbent surface 11a curved inwardly. Therefore, in this case, the excrement receiving structure 1 may not be necessarily supported by the leak-barrier cuffs 14.

FIG. 8 is a view similar to FIG. 4, illustrating an embodiment of the invention. In the diaper 10 according to this embodiment, the transversely opposite edges 8 of the excrement receiving structure 1 are attached not to the leak-proof cuffs 14 but to the topsheet 11 by means of hot melt adhesive 5f. Specifically, the edges 8 respectively defined by parts of the barrier walls 3 made of flexible sheets are bent onto the topsheet 11 and bonded to the topsheet 11. In the diaper 10 according to this embodiment, the excrement receiving structure 1 has its width reduced and the passage 2 also has its diameter in the transverse direction X correspondingly reduced when the liquid-absorbent structure 7 sags downward to reduce an apparent width thereof. However, the excrement receiving structure 1 of a honeycomb construction has a relatively high flexural rigidity and not easily sags even when the liquid-absorbent structure 7 sags. Consequentially, such high flexural rigidity of the excrement receiving structure 1 allows it to create a space between the excrement receiving structure 1 and the sagged topsheet 11.

Figure 9:
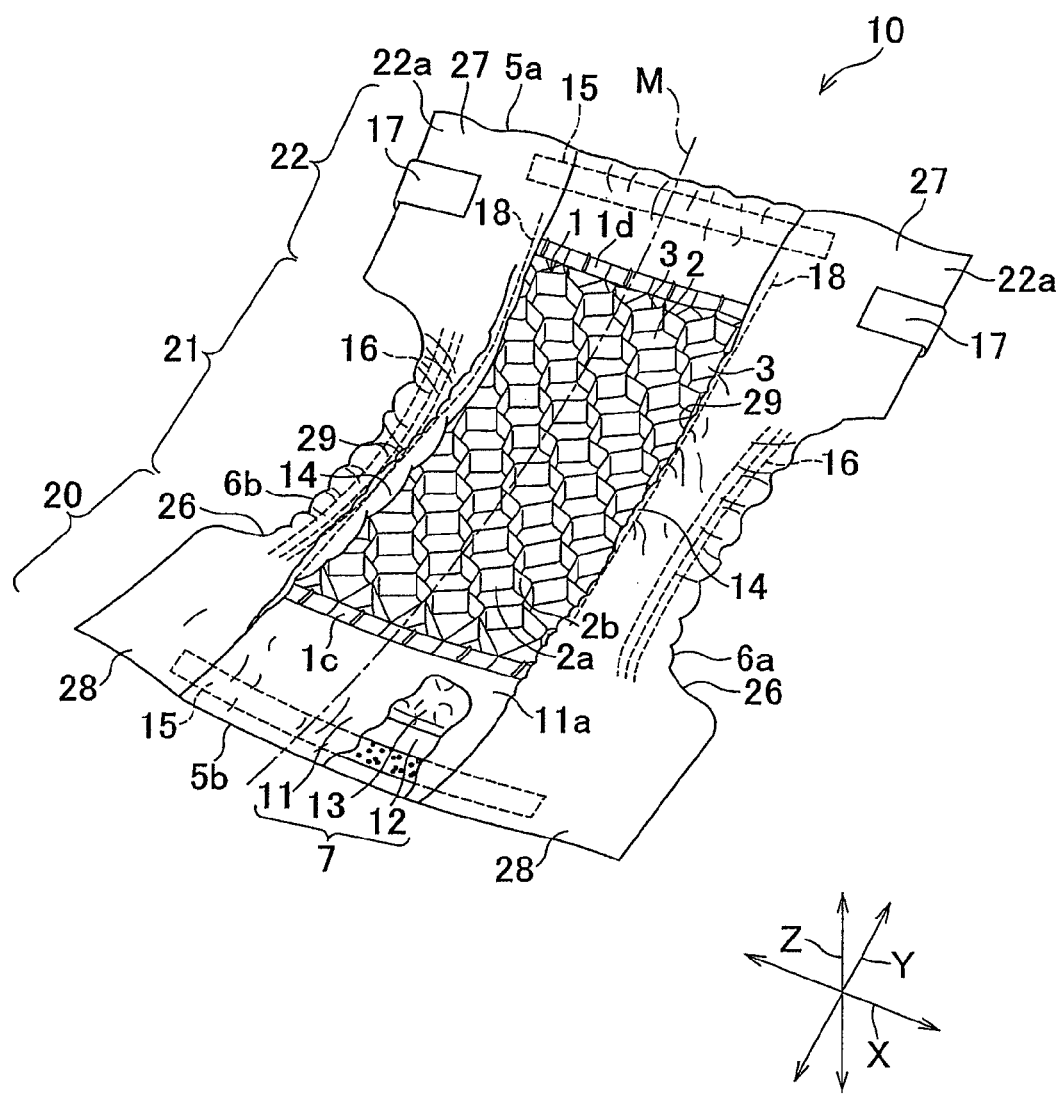
FIG. 9 is a perspective view similar to FIG. 1 to show an embodiment of the present invention.

FIG. 9 is also a view similar to FIG. 1, illustrating an embodiment of the invention. In the case of the diaper 10 shown by FIG. 9, portions of the flexible thin barriers 3 lying on front and rear ends 1c, 1d of the excrement receiving structure 1 are bent onto the topsheet 11 and fixed thereto by means of hot melt adhesive (not shown). Although this excrement receiving structure 1 also is not supported by the leak-barrier cuffs 14, portions of the excrement receiving structure 1 extending between the front and rear ends 1c, 1d can be spaced from the topsheet 11 as the liquid-absorbent structure 7 sags in the longitudinal direction Y. It should be noted that, also for the excrement receiving structure 1 of FIG. 9, the transversely opposite edges 8 thereof underlying the leak barrier cuffs 14 may be bonded to the topsheet 11 in the same manner as in the case illustrated by FIG. 8. As will be apparent from FIGS. 8 and 9, the excrement receiving structure 1 may be bonded along regions thereof opposed in the transverse direction X or along regions thereof opposed in the longitudinal direction Y to the topsheet 11. If it is desired to prevent the excrement receiving structure 1 and the topsheet 11 from being spaced from each other, respective portions of the excrement receiving structure 1 and the topsheet 11 opposed to each other may be bonded together.

Figure 10:
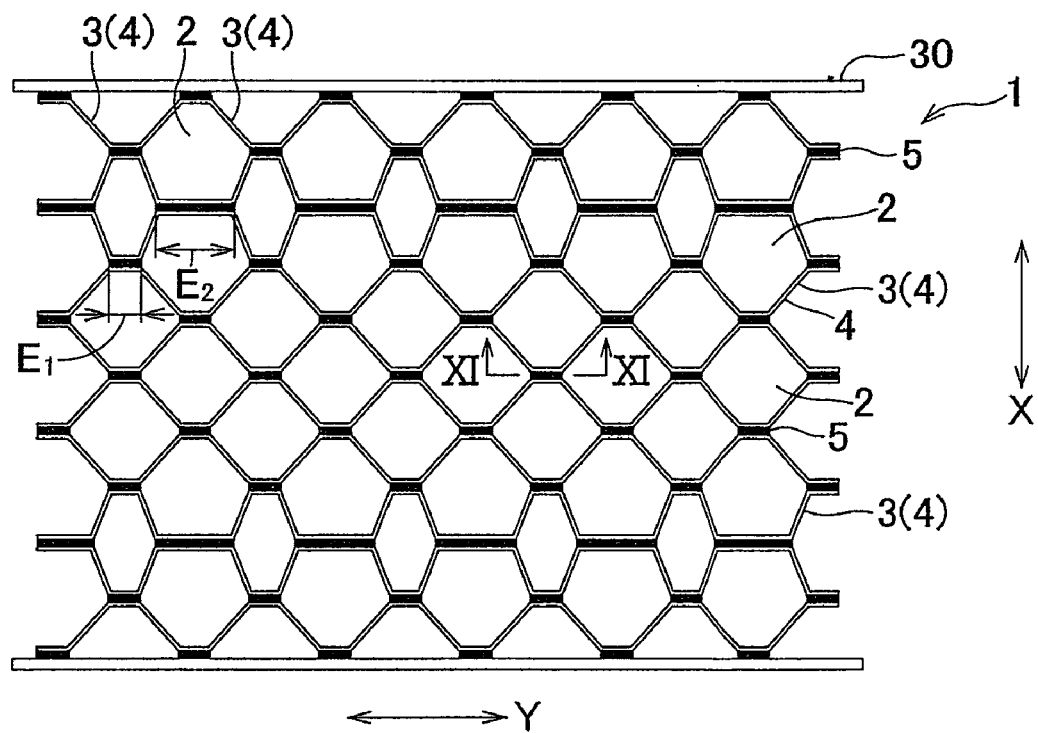
FIG. 10 is a plan view similar to FIG. 3 to illustrate an embodiment of the present invention.

FIG. 10 is a view similar to FIG. 3, illustrating an embodiment of the invention. In the case of this excrement receiving structure 1 as illustrated by FIG. 10, a width E of the adhesive 5 includes two different widths $E_1$ and $E_2$, resulting in two passages of different shapes of the passages 2.

FIG. 11 is a sectional view taken along a line XI-XI in FIG. 10. The hot melt bonding spot 5 on the flexible thin barriers 3 extend over a substantially uniform dimension in the longitudinal direction Y, leaving clearances 5g, 5h between upper and lower edges 1a, 1b of the respective flexible thin barriers 3. The presence of the clearance 5g prevents the bonding spot 5 from unacceptably rubbing up the topsheet 11 and the presence of the clearance 5h prevents the bonding spot 5 from irritating wearer's skin. Preferably the clearances 5g, 5h are dimensioned to be in a range of 0.5 to 3 mm.

FIG. 12 is a view similar to FIG. 11, illustrating an embodiment of the invention. The area of the bonding spot 5 may be gradually enlarged from the upper surface 1b toward the lower surface 1a of the excrement receiving structure 1 to slant the barrier walls 3 defining the passage 2 so that a cross-section of the passage 2 taken in the thickness direction may be funnel-shaped.

Figure 13:
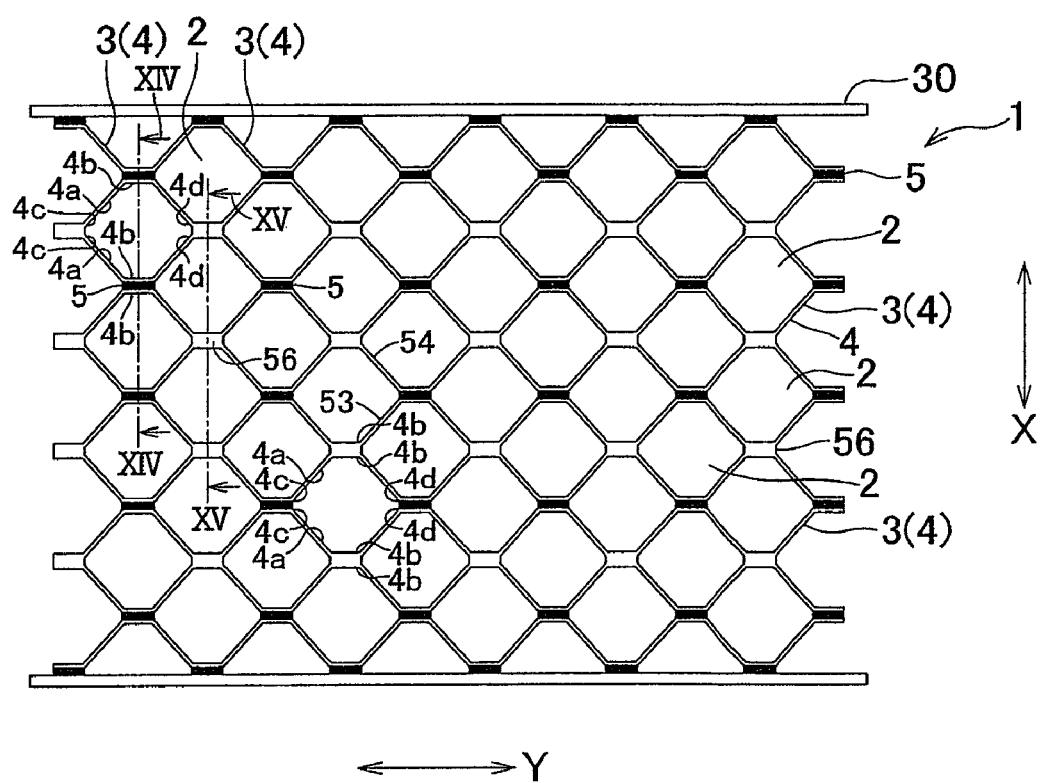
FIG. 13 is a plan view similar to FIG. 3 to illustrate an embodiment of the present invention.
Figure 14:
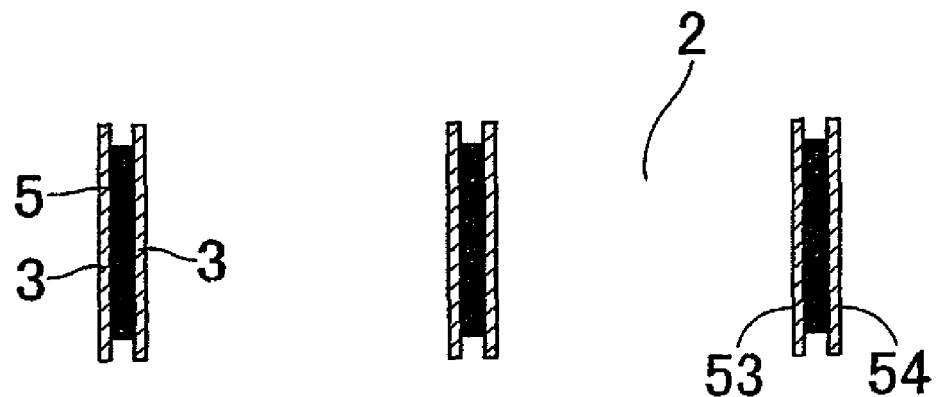
FIG. 14 is a cut surface taken along the line XIV-XIV in FIG. 13.
Figure 15:
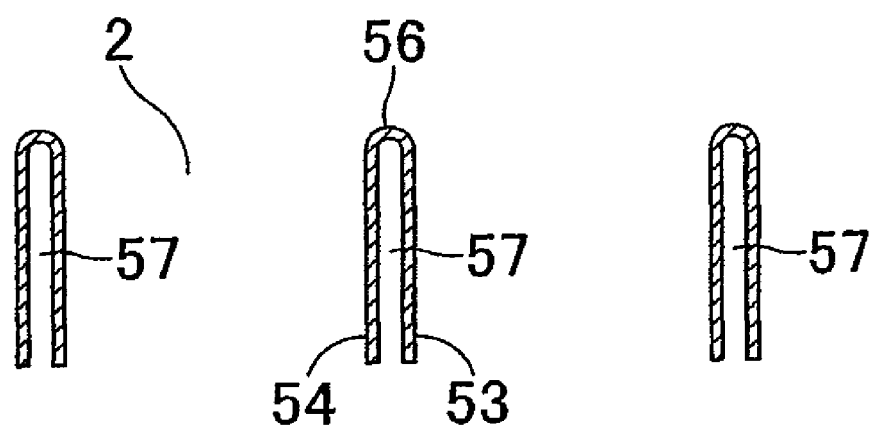
FIG. 15 is a cut surface taken along the line XV-XV in FIG. 13.
Figure 16:
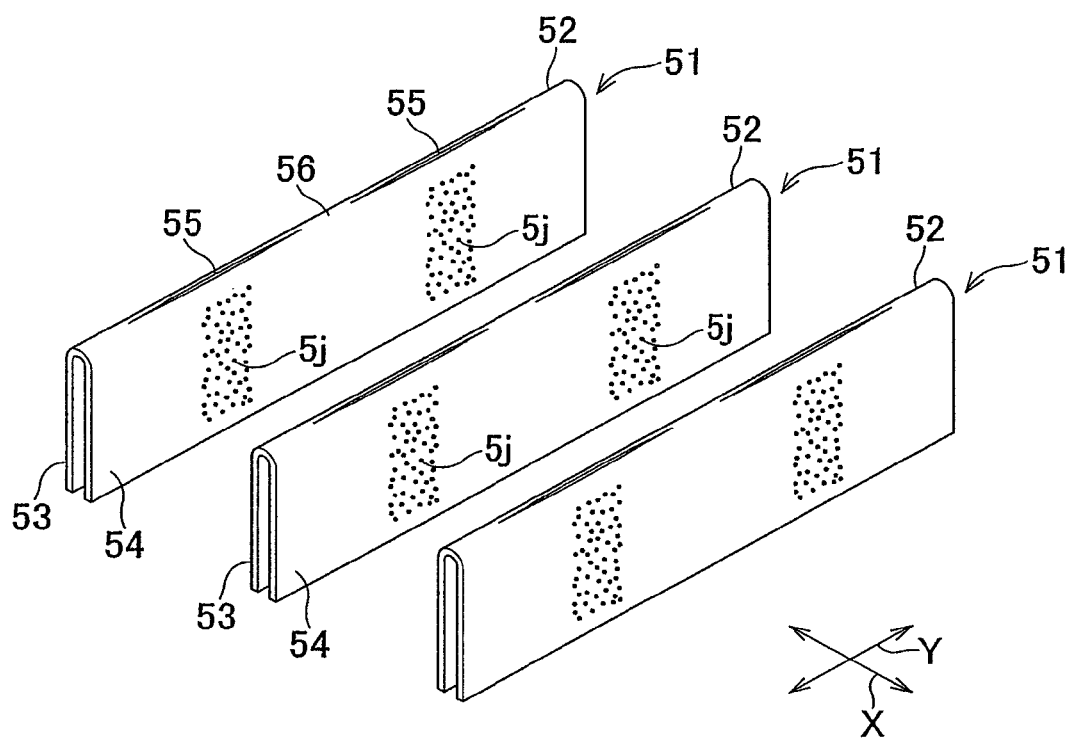
FIG. 16 is a schematic diagram to illustrate a process to prepare an excrement receiving structure.

Of FIGS. 13, 14, 15 and 16, FIG. 13 is a plan view similar to FIG. 3, illustrating the excrement receiving structure 1 according to an embodiment of the invention, FIGS. 14 and 15 are sectional views taken along lines XIV-XIV and XV-XV in FIG. 13, respectively, and FIG. 16 is a perspective view of sheet component 51 forming the excrement receiving structure 1. The sheet component 51 is made of the same material as the flexible sheet strip 4 as shown in FIG. 3 and folded along a folding line 52 extending in the longitudinal direction Y so as to define a first portion 53 and a second portion 54 placed upon each other. The sheet component 51 has slit-segments 55 and slitless segments 56 provided alternately along the folding line 52 wherein the first portion 53 and the second portion 54 are contiguous to each other along the slitless segments 56. The first portion 53 is coated with the adhesive 5j at respective zones corresponding to middles of the respective slit-segments 55 as viewed in the longitudinal direction Y so that a plurality of bonding spots 5 may be formed in the transverse direction X. The first portion 53 and the second portion 54 are placed on and bonded to each other by means of these bonding spots 5 to obtain a composite layer (not shown). Then the composite layer may be stretched in the transverse direction X to open up the slit-segments 55 and simultaneously to space the first and second portions 53, 54 from each other between each pair of the adjacent bonding spots. In this manner, the excrement receiving structure 1 of FIG. 13 is obtained.

In the case of the excrement receiving structure 1 of FIG. 13, opposite V-shaped portions 4a, 4a respectively comprise open ends 4c, 4c and 4d, 4d and closed ends 4b, 4b. Each pair of the open ends 4c and 4c or 4d and 4d may be integrated together by means of the adhesive 5j or by the intermediary of a bridge, i.e. the slitless portion 56. Each pair of the adjacent closed ends 4b, 4b of the V-shaped portions 4a, 4a may be also integrated together by means of the adhesive 5j or by the intermediary of the bridge 56. Both the first portion 53 and the second portion 54 of the sheet component 51 correspond to the flexible sheet strips 4.

Figure 17:
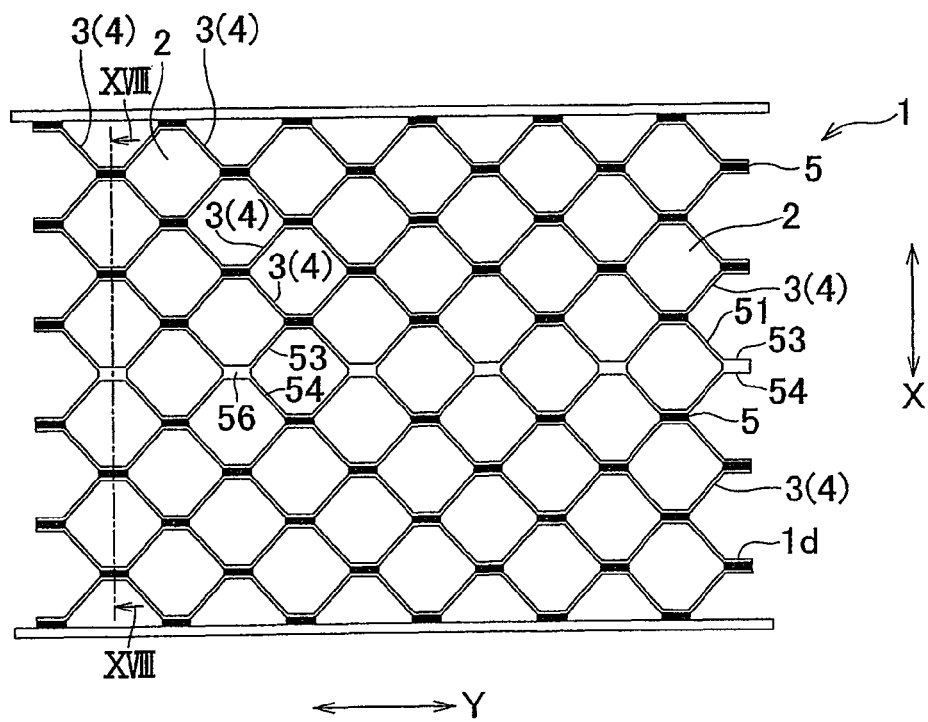
FIG. 17 is a plan view similar to FIG. 3 to illustrate an embodiment of the present invention.
Figure 18:
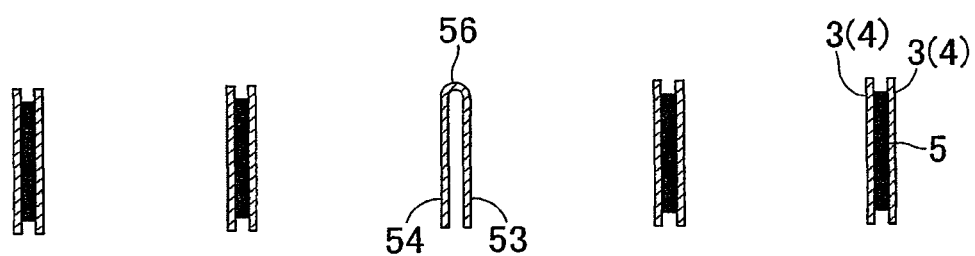
FIG. 18 is a sectional view taken along the line XVII-XVII in FIG. 17.

FIG. 17 is a view similar to FIG. 3, illustrating an embodiment of the invention and FIG. 18 is a sectional view taken along a line XVIII-XVIII in FIG. 17. The excrement receiving structure 1 of FIG. 17 is similar to that of FIG. 3 except that the sheet component 51 of FIG. 16 is used in the middle in the transverse direction X. In the case of the excrement receiving structure 1 of FIG. 17, the first portion 53 and the second portion 54 of the sheet component 51 located in the rear edge 1d of the excrement receiving structure 1 may be spread out in the transverse direction X of the diaper 10 to bond the excrement receiving structure 1 to the topsheet 11.

FIG. 19 is a side view illustrating an apparatus 200 used to measure a flexural stiffness of the stock material for the sheet strip 4 in accordance with the cantilever method. The apparatus 200 comprises a horizontal table section 201, a sloping table section 202 extending at an angle of 45° with respect to the horizontal table section 201 and a holder 203. A test piece 205 having a width of 25 mm and a length of 150 mm is cut out from the stock material for the sheet strip 4. The test piece 205 is placed on the horizontal table section 201 in a manner that one end 205a of the test piece 205 extends toward the sloping table section 202 by a length L beyond a front end 206 of the horizontal table section 201 and held down in this position by the holder 203 from the upper surface 208 of the test piece 205. Then the length L of the test piece 205 extending beyond the front end 206 of the horizontal table section 201 is gradually varied until the one end 205a of the test piece 205 bend due to its own weight and comes in contact with the sloping table section 202. The length L at this moment of contact is determined as the minimum length $L_1$. Then the test piece 205 is reversed and the similar procedure is followed except that the lower surface 209 is held down by the holder 203. The length L at the moment the one end 205a comes in contact with the sloping table section 202 is determined as the minimum length $L_2$. An average value between the length $L_1$ and the length $L_2$ is calculated as the flexural stiffness value.

What is claimed is:

1. A body fluid absorbent wearing article having a longitudinal direction, a transverse direction and a thickness direction, said article comprising:
    a front waist region and a rear waist region extending in said transverse direction, and a crotch region extending between said waist regions in said longitudinal direction;
    an excrement receiving structure extending at least in said crotch region;
    a liquid-absorbent structure having a liquid-absorbent surface adapted to face a wearer's skin;
    wherein
    said excrement receiving structure has a plurality of passages defined by flexible walls; and
    each of said plurality of passages has a first opening facing said liquid-absorbent surface and a second opening facing away from said liquid-absorbent surface; and
    a pair of leak-barrier cuffs extending along lateral edges of said excrement receiving structure in said longitudinal direction,
    wherein
    said pair of leak-barrier cuffs comprise proximal edges permanently attached to said liquid-absorbent surface and elasticized distal edges;
    said excrement receiving structure has transversely opposite sides permanently bonded to said pair of leak-barrier cuffs between said proximal edges and said elasticized distal edges; and
    the excrement receiving structure is suspended at the transversely opposite sides by the leak-barrier cuffs to be separable from the liquid-absorbent surface in the thickness direction.

2. The article defined by claim 1, wherein the transversely opposite sides of said excrement receiving structure are directly attached to said leak-barrier cuffs, respectively, without direct attachment to said liquid-absorbent surface.

3. The article defined by claim 1, wherein said flexible walls are formed from nonwoven fabrics that have fibers oriented in the thickness direction.

4. The article defined by claim 1, wherein said flexible walls are adapted to be folded upon exertion of pressure from the thickness direction.

5. The article defined by claim 1, wherein said flexible walls are bonded to each other in the thickness direction all the way from the first opening to the second opening.

* * * * *